United States Patent [19]

McCoy

[11] Patent Number: 4,543,090
[45] Date of Patent: Sep. 24, 1985

[54] STEERABLE AND AIMABLE CATHETER

[76] Inventor: William C. McCoy, 11339 Valley Meadow Dr., Zionsville, Ind. 46077

[21] Appl. No.: 547,402

[22] Filed: Oct. 31, 1983

[51] Int. Cl.$^4$ ............................................. A61M 25/00
[52] U.S. Cl. ...................................... 604/95; 128/657
[58] Field of Search ................. 604/95, 281, 280, 264; 128/657, DIG. 16

[56] References Cited

U.S. PATENT DOCUMENTS

| | | |
|---|---|---|
| 3,043,309 | 7/1962 | McCarthy . |
| 3,605,725 | 9/1971 | Bentov . |
| 3,674,014 | 7/1974 | Tillander . |
| 3,729,008 | 4/1973 | Berkovits . |
| 3,773,034 | 11/1973 | Burns et al. . |
| 3,890,997 | 6/1975 | Wilson . |
| 4,146,019 | 3/1979 | Bass et al. ............................... 128/6 |
| 4,176,662 | 12/1979 | Frazer . |

Primary Examiner—Stephen C. Pellegrino
Attorney, Agent, or Firm—Barnes & Thornburg

[57] ABSTRACT

A catheter and the like is steerable through cavities within a body and aimable toward organs or tissue within the body. The catheter includes an elongated tubular member having a proximal end and a distal end for insertion into the body and a plurality of temperature-activated memory elements in the distal end of the tubular member. Each memory element assumes a first shape when heated to a predetermined temperature and assumes. Each memory element is coupled to at least one other memory element so that movement of one element results in movement of the other element. Each memory element is moved to a second shape when the memory element coupled thereto is heated to the predetermined temperature. A control system adjacent the proximal end of the tubular member allows an operator to selectively control the temperature of each temperature-activated element to deflect the distal end of the tubular member so as to either direct the course of the tubular member or to direct the distal end of the tubular member toward an organ or tissue within the body. The control system includes a power supply source, electrical connections between the power supply source and the memory elements in the distal end of the tubular member, and a control device for selectively applying power to heat the memory elements to their predetermined temperatures to deflect the distal end of the tubular member so as to steer the tubular member or aim the distal end of the tubular member within the body.

14 Claims, 7 Drawing Figures

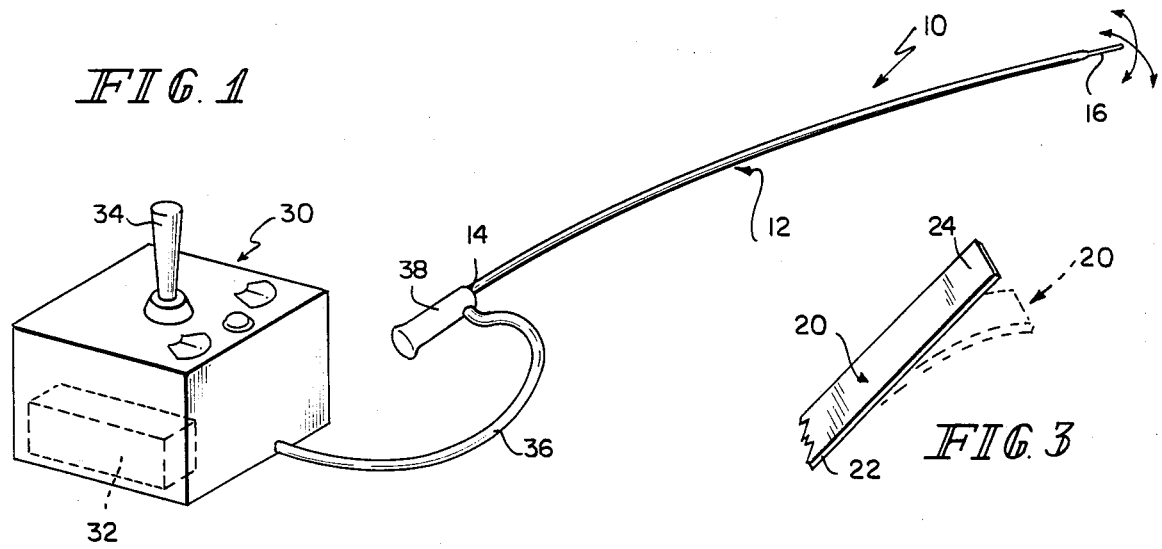
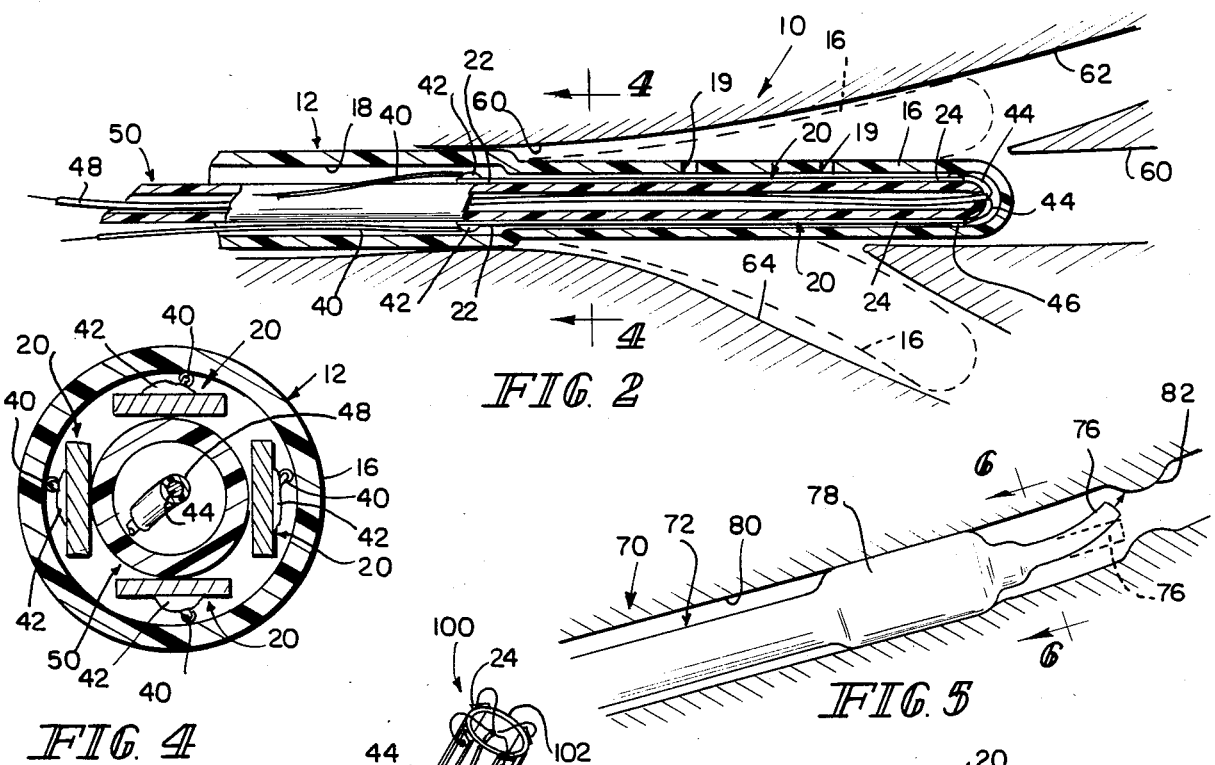
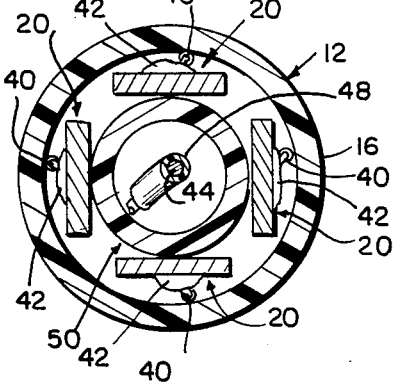
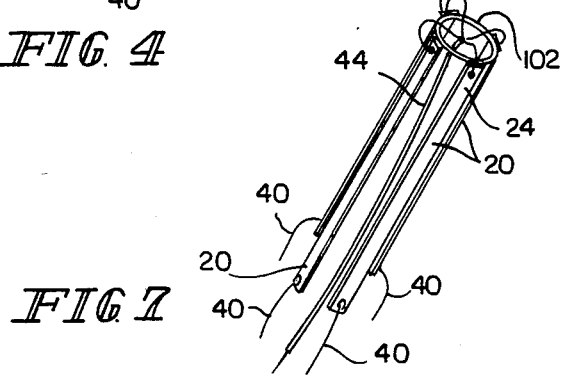
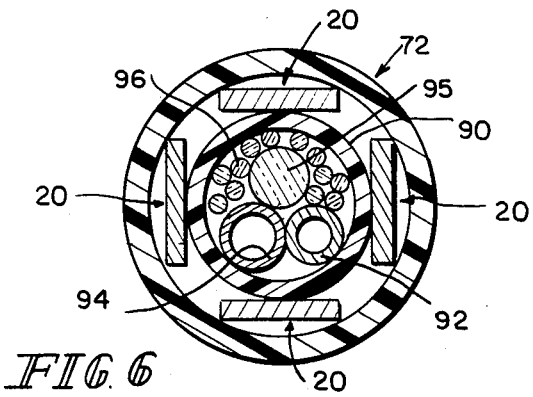

STEERABLE AND AIMABLE CATHETER

The present invention relates to catheters, cannulae, and the like. More particularly, the present invention relates to catheters that are steerable through body cavities and aimable at obstructions, organs, or tissue within the body from a position external to the body.

Some attempts have been made in the past to provide catheters having distal ends which, when inserted into a body, are manipulatable to advance the catheter through body cavities. See for example, U.S. Pat. Nos. 3,674,014 and 3,773,034. The catheter disclosed in U.S. Pat. No. 3,674,014 includes permanent magnets and employs a magnetic field to bend the distal end of the catheter. The catheter disclosed in U.S. Pat. No. 3,773,034 includes fluid conduits and employs a fluid to bend the distal end of the catheter. Other controlled devices are disclosed in U.S. Pat. Nos. 3,605,725 and 4,176,662. However, these prior devices are quite difficult to control and manipulate.

Some work has previously been done to produce a catheter which is readily insertable while being effectively anchorable in a body cavity. See, for example, U.S. Pat. Nos. 3,729,008 and 3,890,977. In U.S. Pat. No. 3,890,977 the distal end of the catheter is formed into a desired shape by using a material exhibiting mechanical memory that is triggered by heat. By heating the mechanical memory material, the distal end of the catheter is shaped to anchor the catheter within the body. However, the change of the shape of the distal end in these prior devices is limited to a single direction.

Other devices are known for guiding a catheter to a particular location within the body. See for example U.S. Pat. No. 3,043,309.

According to the present invention, a catheter has a distal end for ready insertion into a body, a plurality of temperature-activated memory elements in the distal end, each memory element assuming a first shape in response to temperature and being moved to a second shape in response to a force, means for coupling each memory element to at least one other memory element, and control means for controlling the temperature of each memory element from a position adjacent the proximal end of the catheter to deflect the distal end of the catheter in a plurality of directions to steer or aim it within the body.

One object of the present invention is to provide a steerable catheter, cannula, and the like which is easy to operate and steerable in a plurality of different directions within the body.

Another object of the present invention is to provide an aimable catheter, cannula, and the like which is easy to operate and which can be aimed at obstructions, organs, or tissues in a plurality of different directions within the body.

Yet another object of the present invention is to provide a catheter, cannula, and the like which is aimable to direct the course of fluid, light, medical instruments or a laser beam within the body.

Various other features and advantages of the present invention will become apparent in view of the following detailed description of embodiments thereof representing the best mode of carrying out the invention as presently perceived, which description should be considered in conjunction with the accompanying drawings, in which:

FIG. 1 is a perspective view of a steerable and aimable catheter, cannula, and the like embodying the present invention;

FIG. 2 is a longitudinal cross-sectional view, partly broken away, of a body cavity and the distal end of the catheter, cannula, and the like shown in FIG. 1;

FIG. 3 is a perspective view of an embodiment temperature-activated memory element employed in the catheter, cannula, and the like showing its different shapes;

FIG. 4 is a transverse cross-sectional view of the distal end of the catheter, cannula, and the like embodying the present invention taken generally along section lines 4—4 in FIG. 2;

FIG. 5 is a longitudinal cross-sectional view of a body cavity showing the aimable feature of a catheter, cannula, and the like embodying the present invention;

FIG. 6 is a transverse cross-sectional view of the embodiment of the catheter, cannula, and the like shown in FIG. 5 taken generally along section lines 6—6 of FIG. 5; and FIG. 7 is a perspective view of an embodiment of a plurality of temperature-activated memory elements employed in the distal end of the catheter, cannula, and the like to deflect or move the distal end for steering and aiming thereof.

A catheter 10 embodying the present invention is generally shown in FIG. 1. Catheter 10 includes an elongated tubular member 12 having a proximal end 14 and a steerable and aimable distal end 16. In the illustrative embodiment, the tubular member 12 is formed of plastic, Teflon, or cross-linked kynar or polyethylene. As will become apparent in the description of catheter 10, it is desirable that tubular member 12 be formed of a material that is flexible, that can withstand heat, and which provides electrical insulation.

As best shown in FIG. 2, the tubular member 12 can have a lumen 18 for the passage of fluid from the proximal end 14 to the distal end 16 and vice versa. Typically, the tubular member 12 includes one or more holes or openings 19 through which fluids are either injected into or drained from a body cavity. Some cannulae may have an open distal end 16 for insertion and withdrawal of medical instruments.

As shown in FIGS. 2 and 3, a plurality of temperature-activated memory elements 20 are incorporated into the distal end 16 of the tubular member 12. It may be desirable to isolate the memory elements 20 from the body cavity. The temperature-activated memory elements 20 preferably exhibit a memory characteristic in response to temperature changes. The elements 20 may be wires or flat strips such as shown in FIG. 3. In the illustrative embodiment, the temperature-activated memory elements 20 are formed of a mechanical memory metal such as a nickel titanium alloy. While a nickel titanium alloy is desirable, other metal elements having a memory characteristic related to temperature could be used without departing from the scope of the invention. Such metal elements should have a high resistance to electric current so that heat is produced when current is passed therethrough.

As shown in FIG. 3, the elements 20 have a proximal end 22 and a distal end 24. Each element 20 has a first shape represented by the broken lines in FIG. 3 and a second shape represented by the solid lines in FIG. 3. Illustratively, the first shape is an arcuate shape, and the second shape is a straight shape. It will be appreciated that the first shape could be any shape.

Each temperature-activated memory element 20 is originally annealed into its first or preset shape (represented by the broken lines in FIG. 3). Memory elements 20 are cooled and straightened to their second shape (represented by the solid lines in FIG. 3) before incorporation into the distal end 16 of the tubular member 12. When the elements 20 are again heated to a predetermined transitional temperature they return to their first or preset shape. By applying an opposing force to an element 20 that has assumed its preset shape it can be moved to its second shape (represented by the solid lines in FIG. 3). In the illustrative embodiment, the predetermined transitional temperature is any temperature above body temperature. For example, the predetermined transitional temperature may be in the range of 100° to 150° F.

The elements 20 can either be directly incorporated into the distal end 16 of the tubular member 12 or can be carried on an electrically insulative core 50. As will be discussed later, each memory element 20 must be coupled to at least one other memory element 20 so that when one of the memory elements is heated it applies a force to the other memory element 20.

The catheter 10 further includes an electronic control system 30 for controlling current flow to vary the temperature of each temperature-activated memory element 20 from a position external to the body so as to deflect the distal end 16 of the tubular member 12 in a plurality of different directions corresponding to the first shapes of the elements 20. The control system 30 includes a power supply source 32 which may be either AC or DC. The system 30 also includes a control device 34 which, in the illustrative embodiment, is similar to a "joystick" control, tactile membrane switch, or ball controller. It will be appreciated that various types of control devices 34 may be employed without departing from the scope of the present invention.

The power supply source 32 is coupled through control device 34 to the tubular member 12 by cable 36 and a coupling device 38. Further, the temperature-activated memory elements 20 are electrically connected to the control device 34 through cable 36 and coupling 38 by electrical wires 40 which are attached to the proximal ends 22 of elements 20 by conventional means 42 such as soldering or crimping. Return or ground wires 44 are attached to the distal ends 24 of elements 20 by conventional means such as soldering or crimping 46. Return or ground wires 44 may be combined into a single ground cable 48 as shown in FIG. 2. In the embodiment illustrated in FIG. 2, the temperature-activated memory elements 20 are carried on the exterior of the core 50 and ground wire 48 runs through the interior of the core 50. Core 50 couples each memory element 20 to at least one other memory element 20 so that when a memory element 20 assumes its first shape in response to heat it applies a force to the other memory element 20 coupled thereto. Other mounting arrangements could be used for incorporating the memory elements 20 into the distal end 16 of the tubular member 12 without departing from the scope of the present invention.

In operation, the distal end 16 of the tubular member 12 is inserted into a body cavity 60 such as a blood vessel while memory elements 20 are straight and at a temperature below the transitional temperature. At this stage, each memory element 20 in its second shape for ready insertion of the distal end 16 into the body cavity 60. The tubular member 12 is pushed through cavity 60 until it reaches a desired branch 62 or 64 extending from the cavity 60. Control device 34 is manipulated to apply an electrical voltage or current to one or more of the memory elements 20. Because of the high resistance of memory elements 20, heat is generated. When a memory element reaches its predetermined transitional temperature (i.e., a predetermined temperature above body temperature) the memory element 20 assumes its first shape (as shown by the broken lines in FIG. 3), thereby deflecting or moving the distal end 16 of tubular member 12 into one of the desired branch cavities 62 or 64. Once the distal end 16 is in the branch 62 or 64, power can be removed from the memory element 20 to allow it to cool. While the memory element 20 is at a temperature above its predetermined transitional temperature it remains relatively stiff in its first shape. When the memory element 20 cools to a temperature below its predetermined transitional temperature it becomes soft or pliable in its first shape. After cooling, a voltage or current is applied to another memory element 20 coupled to the cooled memory element 20 still in its first shape. When the other memory element 20 reaches its predetermined transitional temperature, it begins to assume its first shape and in doing so applies a force to the memory element 20 coupled thereto to move it to its second shape (as shown by the solid lines in FIG. 3). The catheter tubular member 12 can continue to be pushed through the branch 62 or 64 until it is again desirable to turn or bend the catheter 10.

As illustrated in FIG. 4, four temperature-activated memory elements 20 may be carried on the exterior of core 50. In the illustrative embodiment, pairs of the memory elements 20 are shown diametrically opposed to each other so that opposed elements 20 apply forces to each other when they are heated. Thus, the distal end 16 may be deflected in at least four different directions by applying an electrical current or voltage to one of the memory elements 20. It will be appreciated that more or less than four memory elements 20 may be utilized without departing from the scope of the present invention. However, it should be noted that at least two memory elements 20 are required. Further, it may be desirable to apply an electrical voltage or current to more than one of the memory elements 20 simultaneously to increase the number of directions in which the distal end 16 of the tubular member 12 may be deflected. The control system 30 may include means for regulating the application of current or voltage applied to the memory elements 20 to allow virtually an unlimited number of directions in which the distal end 16 may be deflected for the purpose of steering the catheter tubular member 10 through body cavities. It will be appreciated that a large number of wire memory elements could be incorporated into the distal end 16 and a voltage or current applied to one or more of the wires to deflect the distal end 16 in a desired direction.

Another application for a catheter 70 embodying the present invention is shown in FIGS. 5 and 6. Reference numerals from FIGS. 1-4 have been applied to the catheter 70 shown in FIGS. 5 and 6 where the same or similar parts are being used. Catheter 70 includes a tubular member 72 having a distal end 76. The distal end 76 includes a plurality of temperature-activated memory elements 20 of the type previously described. The same or similar control system may be employed in connection with the catheter 70 in a body cavity 80 for the purpose of aiming the distal end 76 at an obstruction, organ, or tissue 82 within the cavity 80. The catheter 70 may be anchored in the cavity 80 by a balloon 78. Once the catheter 70 is anchored, the distal end 76 is aimed in one of a plurality of directions to establish a course for the injection of fluid or a laser beam at the organ or tissue 82.

As shown in FIG. 6, a core 90 formed of insulative material passes through tubular member 72. Memory elements 20 are carried on the core 90 between the core 90 and the tubular member 72. Core 90 serves to couple each memory element 20 to at least one other memory element 20 in the manner and for the purpose previously described. The hollow core 90 may include a first tube 92 for carrying a fluid from the proximal end of the catheter 70 to the distal end 76. A return tube 94 may be included for extracting fluid. It will be appreciated that either passage 92 or 94 may be used for inserting a medical instrument into the cavity 80. Core 90 may also include a transparent member 95 providing a lens for observing the obstruction, organ, or tissue 82 and a bundle of fiber-optic lines 96 for transmitting light or a laser beam to the distal end 76. Thus, in the embodiment illustrated in FIGS. 5 and 6, catheter 70 has a distal end 76 which is aimable in a plurality of directions in accordance with the present invention for the purpose of establishing a course for the injection of fluid, light, or a laser beam at an obstruction, organ, or tissue 82.

Another embodiment of an arrangement for the memory elements 20 is shown in FIG. 7. The memory element arrangement 100 includes a plurality of memory elements 20 coupled at their distal ends 24 by a thermally and electrically insulative ring 102. Various materials, such as plastic, may be used to construct the ring 102. Ground wires from each memory element 20 are channeled through a common ground wire conduit 44. Ring 102 serves to couple the memory elements 20 to each other and performs a function similar to cores 50 and 90. This arrangement facilitates the mounting of the memory elements 20 in the distal end 16, 76 of the catheters 10, 70, respectively.

While illustrative embodiments and uses of catheters, cannulae, and the like embodying the present invention have been shown and described, it will be appreciated that various modifications may be made to the illustrative embodiments without departing from the scope of the present invention.

What is claimed is:

1. A catheter comprising an elongated tubular member having a proximal end and a distal end for insertion into a body, at least two temperature-activated memory elements in the distal end of the tubular member, each memory element moving to assume a predetermined shape when heated to a predetermined temperature, the memory elements being disposed in the distal end of the tubular member so that they move in different directions to assume their predetermined shapes, means for coupling one memory element to another memory element so that when the one memory element moves in a first direction to assume its predetermined shape a force is applied to move the other memory element in the first direction and when the other memory element moves in a second direction to assume its predetermined shape a force is applied to move the one memory element in the second direction, and control means for heating selectively each memory element to the predetermined temperature so that the one memory element assumes its predetermined shape and the other memory element is moved to deflect the distal end of the tubular member in the first direction and so that the other memory element assumes its predetermined shape and the one memory element is moved to deflect the distal end of the tubular member in the second direction.

2. The catheter of claim 1 wherein the predetermined shape is a curved shape.

3. The catheter of claim 2 wherein the distal end of the tubular member is formed of flexible non-conductive material and each memory element is formed of a metal having a relatively high electrical resistance.

4. The catheter of claim 3 wherein the control means includes a power supply source, means for coupling the power supply source to the memory elements, and a control device for selectively applying power to heat the memory elements to their predetermined temperatures to steer the distal end of the tubular member through cavities in the body.

5. The catheter of claim 3 wherein the tubular member includes means providing a passageway therethrough and the memory elements are disposed exterior to the passageway in the distal end of the tubular member.

6. The catheter of claim 5 wherein the tubular member further includes light-transmitting means in the passageway for transmitting light from the proximal end to the distal end of the tubular member.

7. The catheter of claim 6 wherein the control means includes a power supply source, means for coupling the power supply source to the memory elements, and a control device for selectively applying power to heat the memory elements to their predetermined temperatures to aim the distal end and light-transmitting means of the tubular member at a desired object in the body.

8. The catheter of claim 7 wherein the memory elements are formed of a nickel titanium alloy.

9. The catheter of claim 8 wherein the tubular member further includes fluid-transmitting means in the passageway for transmitting fluid from the proximal end to the distal end of the tubular member and vice versa.

10. The catheter of claim 3 wherein the two memory elements are located in diametrically opposed relationship to each other in the distal end of the tubular member.

11. The catheter of claim 3 further comprising four memory elements in the distal end of the tubular member and wherein the control means includes means for selectively applying an electrical current to each memory element to deflect the distal end of the tubular member in at least four different directions inside the body.

12. The catheter of claim 11 wherein two of the memory elements are coupled in diametrically opposed relationship to each other in the distal end of the tubular member.

13. A catheter for insertion into a body cavity comprising an elongated tubular member having a proximal end and a distal end for insertion into the body cavity, at least two temperature-activated memory elements in the distal end of the tubular member, each memory element moving to assume a predetermined shape when heated to a predetermined temperature, the memory elements being disposed in the distal end of the tubular member so that they move in different directions to assume their predetermined shapes, means for coupling a first memory element to a second memory element so that when the first memory element moves in a first direction to assume its predetermined shape a force is applied to move the second memory element in the first direction and when the second memory element moves in a second direction to assume its predetermined shape a force is applied to move the first memory element in the second direction, a power supply source, and means for applying power selectively to each of the memory elements to heat them to the predetermined temperature so that the first memory element assumes its predetermined shape and the second memory element is moved to deflect the distal end of the tubular member in the first direction and so that the second memory element assumes its predetermined shape and the first memory element is moved to deflect the distal end of the tubular member in the second direction.

14. A catheter comprising an elongated tubular member having a distal end for insertion into a body, at least two thermally independent temperature-activated memory elements aligned in spaced-apart relation to the distal end of the tubular member, each memory element moving to assume a predetermined shape when heated to a predetermined temperature, the memory elements being disposed in the distal end of the tubular member so that they move in different directions to assume their predetermined shapes, interconnecting means for connecting one memory element to another memory element so that when the one memory elements moves in a first direction to assume its predetermined shape a force is applied to move the other memory element in the first direction and when the other memory element moves in a second direction to assume its predetermined shape a force is applied to move the one memory element in a second direction and for thermally insulating the memory elements from each other so that the temperature of the one memory element is generally unaffected by heating the other memory element and vice versa, and control means for heating selectively each memory element so that the one memory element assumes its predetermined shape and the other memory element is moved to deflect the distal end of the tubular member in the first direction and so that the other memory element assumes its predetermined shape and the one memory element is moved to deflect the distal end of the tubular member in the second direction.

* * * * *